United States Patent [19]
Minerovic et al.

[11] Patent Number: 5,997,814
[45] Date of Patent: Dec. 7, 1999

[54] MULTI-COMPARTMENT PLASTIC WOVEN MESH DRY CHEMISTRY CONTAINER

[75] Inventors: David E. Minerovic, Concord; Christopher M. Fricker, Mentor, both of Ohio; Todd A. Christopher, New Palestine, Ind.; Brian E. Schindly, Mentor; Karen Thomas, Eastlake, both of Ohio

[73] Assignee: Steris Corporation, Mentor, Ohio

[21] Appl. No.: 09/002,096

[22] Filed: Dec. 31, 1997

Related U.S. Application Data

[60] Provisional application No. 60/068,654, Dec. 23, 1997.

[51] Int. Cl.$^6$ ........................................................ A61L 9/00
[52] U.S. Cl. .......................... 422/29; 206/221; 206/538; 422/102; 422/261; 422/266; 422/292; 422/294
[58] Field of Search ............................ 422/29, 292, 294, 422/102, 261, 266; 206/538, 221, 568, 531, 467, 506

[56] References Cited

U.S. PATENT DOCUMENTS 4,171,340  10/1979  Nishimura et al. .................... 422/36
5,662,866   9/1997  Siegel et al. ............................ 422/29

FOREIGN PATENT DOCUMENTS 0 543 591 A1  11/1992  European Pat. Off. .
WO 97/11723   4/1997  WIPO .

*Primary Examiner*—Krisanne Thornton
*Attorney, Agent, or Firm*—Fay, Sharpe, Fagan, Minnich & McKee, LLP

[57] ABSTRACT

An outer, first cup portion having a peripheral wall which has an opening at a first end and at a second end. An inner, second cup portion having a region which is formed from a first material which is impermeable to the powdered reagents but is permeable to water and to solutions containing dissolved reagents, the first and second cup portions being configured such that the second cup portion peripheral wall abuts and is connected to the first end of the outer first cup portion, the first and second being configured such that a first powdered reagent receiving chamber is defined in the first cup portion for receiving a first reagent and a second powdered reagent receiving chamber is defined in the second cup portion for receiving a second reagent, a closure secured to and closing the second end of the outer first cup portion, the closure being impermeable to the first reagent.

27 Claims, 5 Drawing Sheets

MULTI-COMPARTMENT PLASTIC WOVEN MESH DRY CHEMISTRY CONTAINER

This application claims the benefit of the Dec. 23, 1997, filing date of Provisional Application Ser. No. 60/068,654.

BACKGROUND OF THE INVENTION

The present invention relates to the decontamination arts. It finds particular application in conjunction with sterilizing or disinfecting medical instruments and equipment and will be described with particular reference thereto. It should be appreciated, however, that the invention is also applicable to a wide variety of technologies in which at least two components or reagents are kept separate until time of use and then combined through dissolution in a common solvent.

Decontamination connotes the removal of hazardous or unwanted materials, such as bacteria, mold spores, other pathogenic life forms, radioactive dust, and the like. Disinfection connotes the absence of pathogenic life forms. Sterilization connotes the absence of all life forms, whether pathogenic or not.

Heretofore, medical equipment and instruments have often been sterilized in a steam autoclave. Autoclaves kill life forms with a combination of high temperature and pressure. However, steam autoclaves have several drawbacks. The high temperature pressure vessels tend to be bulky and heavy. The high temperature and pressure tends to curtail the useful life of endoscopes, rubber and plastic devices, lenses, and portions of devices made of polymeric materials and the like. Moreover, a typical autoclave sterilizing and cool down cycle is sufficiently long that multiple sets of the medical instruments are commonly required.

Instruments which cannot withstand the pressure or temperature of the oven autoclave are often sterilized with ethylene oxide gas, particularly in larger medical facilities or hospitals. However, the ethylene oxide sterilization technique also has several drawbacks. First, the ethylene oxide sterilization cycle tends to be even longer than the steam autoclave cycle. Another drawback is that ethylene oxide sterilization is sufficiently sophisticated that trained technicians are commonly required, making it unsuitable for physician and dental offices and for other smaller medical facilities. Moreover, some medical equipment can not be sterilized with ethylene oxide gas.

Liquid disinfection systems have also been utilized for equipment which could not withstand the high temperatures of steam sterilization. Commonly, a technician mixes a liquid disinfectant composition and manually immerses the items to be decontaminated. The high degree of manual labor introduces numerous uncontrolled and unreported variables into the process. There are quality assurance problems with the weakening of the disinfectant chemicals due to aging on the shelf, and technician errors in the mixing of sterilants, control of immersion times, rinsing of residue, exposure to the ambient atmosphere after the rinsing step, and the like.

U.S. Pat. No. 5,662,866 to Siegel, et al. discloses a two-compartment cup for powdered sterilant reagent components. An outer cup holds a first reagent while an inner cup, disposed within the outer cup, holds a second reagent. Peripheral walls of inner and outer cups are affixed together at their open ends at flanges. A permeable sheet is affixed to the inner cup portion flange for ventedly sealing both cups. The outer cup is closed at its base by a first detachable base and the inner cup similarly closed by a second detachable base. In use, the two bases are opened to allow mixing of the two reagents. The two-compartment cup ensures sterilization with a reproducible, pre-measured dose of reagents, while also facilitating handling and shipping of the reagents.

The present invention provides for a new and improved two compartment cup or packaging assembly which does not require a second removable base and which is ideal for storing powdered reagents which are retained separately until time of use and are released in solution when a solvent is passed through both compartments.

SUMMARY OF THE INVENTION

In accordance with one aspect of the present invention, a multi-compartment package for holding powdered reagents which interact with water to form an anti-microbial solution is provided. The package includes an outer, first cup portion having a first peripheral wall which has a first opening at a first end and a second opening at a second end, a detachable base portion secured to the second end of the outer first cup portion and closing the second opening, the detachable base portion being detachable by applying a force to the detachable base portion.

The package further includes an inner, second cup portion having a second peripheral wall, an overhanging flange connected at an upper end thereof, a top cover at least partially covering the flange.

The first and second cup portions are configured such that the second cup portion flange abuts and is connected to the first end of the outer first cup portion. The cup portions are also configured such that a first reagent receiving chamber is defined in the first cup portion and a second chamber is defined in the second cup portion.

The second cup portion includes at least a region formed from a material which is impermeable to the received reagents but is permeable to water and to solutions containing dissolved reagents.

In accordance with another aspect of the present invention, a two compartment package for holding powdered reagents which interact in water to form an anti-microbial solution is provided. The package comprises an outer first cup portion having a first peripheral wall which has a first opening at a first end and a second opening at a second end.

The package further comprises an inner second cup portion having an overhanging flange connected at one end. The second cup portion includes a region of a filter material which is permeable to water and solutions. A first powdered reagent receiving chamber is defined in the first cup portion and a second chamber is defined in the second cup portion. The filter material holds first powdered reagents without passing the first reagents to the first chamber and without passing second reagents to the second chamber. One of the chambers holds an acid precursor and the other chamber holds a persalt.

In accordance with yet another aspect of the present invention, a multi-compartment package for holding powdered reagents which interact with water to form an anti-microbial solution is provided. The package includes an outer, first cup portion having a peripheral wall which has an opening at a first end and at a second end. The package further includes an inner, second cup portion having a second peripheral wall and a base wall. At least the second cup portion base wall includes a region which is formed from a material which is impermeable to the powdered reagents but is permeable to water and to solutions containing dissolved reagents.

The first and second cup portions are configured such that the second cup portion peripheral wall abuts and is connected to the outer first cup portion adjacent the first end of the first peripheral wall. The first and second peripheral walls and the second cup base wall are configured such that a first powdered reagent receiving chamber is defined in the first cup portion for receiving a first reagent and a second powdered reagent receiving chamber is defined in the second cup portion for receiving a second reagent. A closure is secured to and closing the second end of the outer first cup portion. The closure is impermeable to the first reagent.

In accordance with another aspect of the present invention, a method is provided. The method comprises providing a first cup having a first cup peripheral wall which has an opening at a first end and is closed by a detachable base wall at a second end and metering a preselected volume of a first powdered reagent into the first cup.

The method further comprises inserting a second cup into the first cup, the second cup including a flange at one end and a region formed from a material which is impermeable to the first powdered reagent and to a second powered reagent but is permeable to water and to solutions containing dissolved reagents, the first and second cups being configured such that when the second cup is inserted into the first cup, the second cup flange abuts the first cup open end.

The method further comprises connecting the second cup flange to the first cup first end, metering a preselected volume of the second powdered reagent into the second cup and sealing a top cover to the second cup flange surrounding the second cup such that the first and second cups are sealed concurrently.

In accordance with another aspect of the present invention, a method is provided, comprising metering a preselected volume of a first powdered reagent into a first cup having a first cup peripheral wall which has an opening at a first end and a second opening closed by a closure at a second end, the closure being impermeable to the first powdered reagent.

The method further comprises metering a preselected volume of a second powdered reagent into a second cup having a flange connected at a first end of the second cup and a region formed from a material which is impermeable to the first and second powdered reagents but is permeable to water and to solutions containing dissolved reagents, the first and second cups being configured such that when the second cup is inserted into the first cup, the second cup flange abuts the first cup open end.

The method also comprises connecting the second cup flange to the first cup first end and sealing a top cover to the second cup flange surrounding the second cup.

In accordance with another aspect of the present invention, a decontamination system is provided. The system comprises a powdered reagent cup receiving well. The system further comprises a first fluid flow path defined between a water receiving inlet and the reagent cup receiving well to bring water from the inlet to the well to mix with powdered reagents and form a decontaminant solution.

The system also comprises a second fluid flow path which is defined for the decontaminant solution from the reagent cup receiving well to a decontamination region for receiving items to be decontaminated. The system further comprises a fluid circulator for selectively circulating fluid through the first and second fluid flow paths and among the inlet, the decontamination region, and the reagent cup receiving well.

Further, the system comprises a multi-chamber powdered decontamination reagent holding cup for insertion into the well. The cup includes an outer, first cup portion having a peripheral wall which has an opening at a first end and at a second end. The cup also includes an inner, second cup portion having a region which is formed from a material which is impermeable to the powdered reagents but is permeable to water and to solutions containing dissolved reagents. The first and second cup portions are configured such that the second cup portion abuts and is connected to the first end of the outer first cup portion. The cups are also configured such that a first powdered reagent receiving chamber is defined in the first cup portion for receiving a first reagent and a second powdered reagent receiving chamber is defined in the second cup portion for receiving a second reagent. A closure is secured to and closes the second end of the outer first cup portion. The closure is impermeable to the first reagent.

One advantage of the present invention is that it facilitates materials handling.

Another advantage of the present invention is that it simplifies filling and sealing of two reagents in separate compartments.

Another advantage of the present invention is that it promotes thorough mixing of the reagents and complete dissolution of the reagents.

Another advantage of the present invention is that undissolved particles of reagent remain trapped within the cup.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
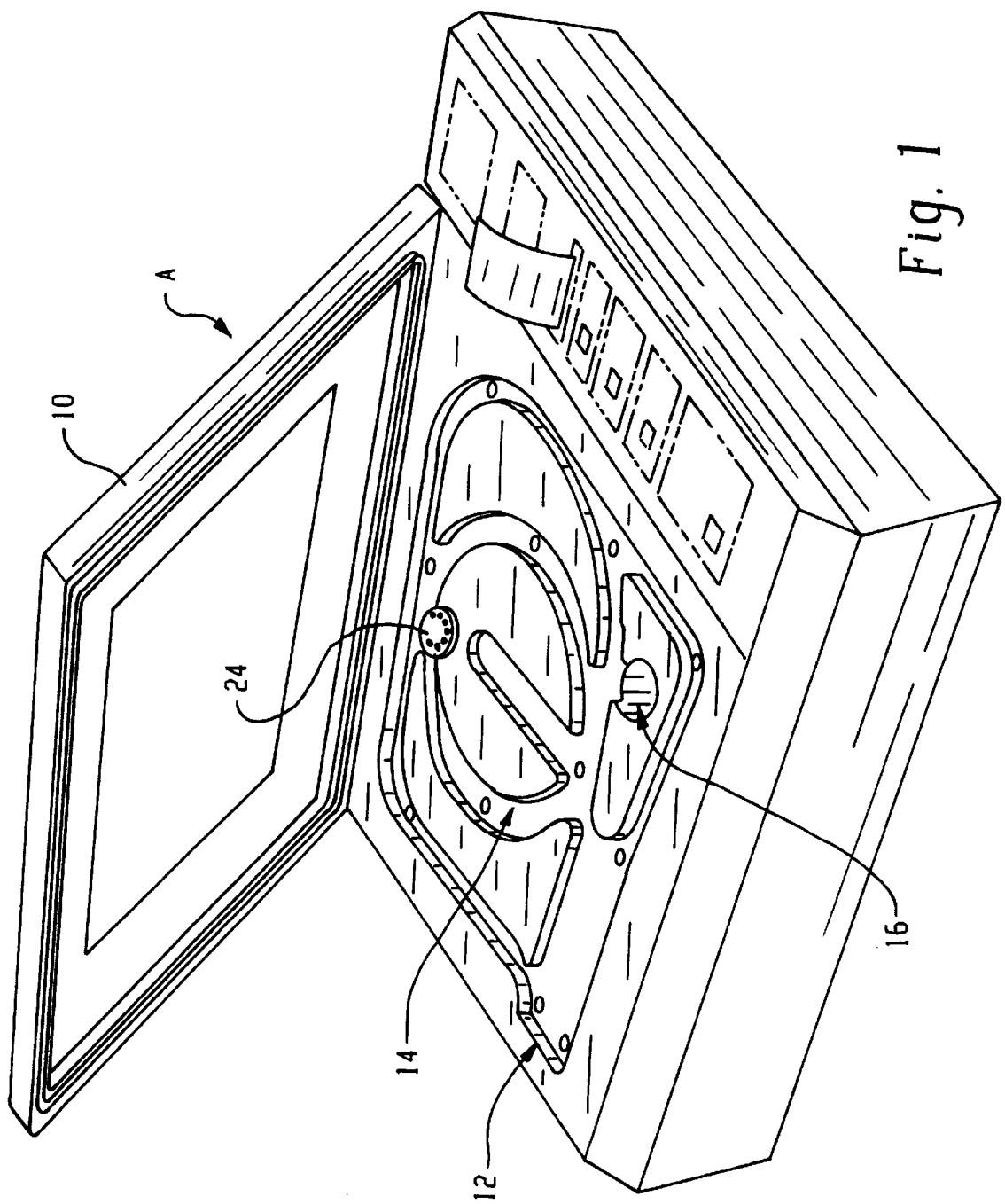
FIG. 1 is an exterior view of a decontamination unit.
Figure 2:
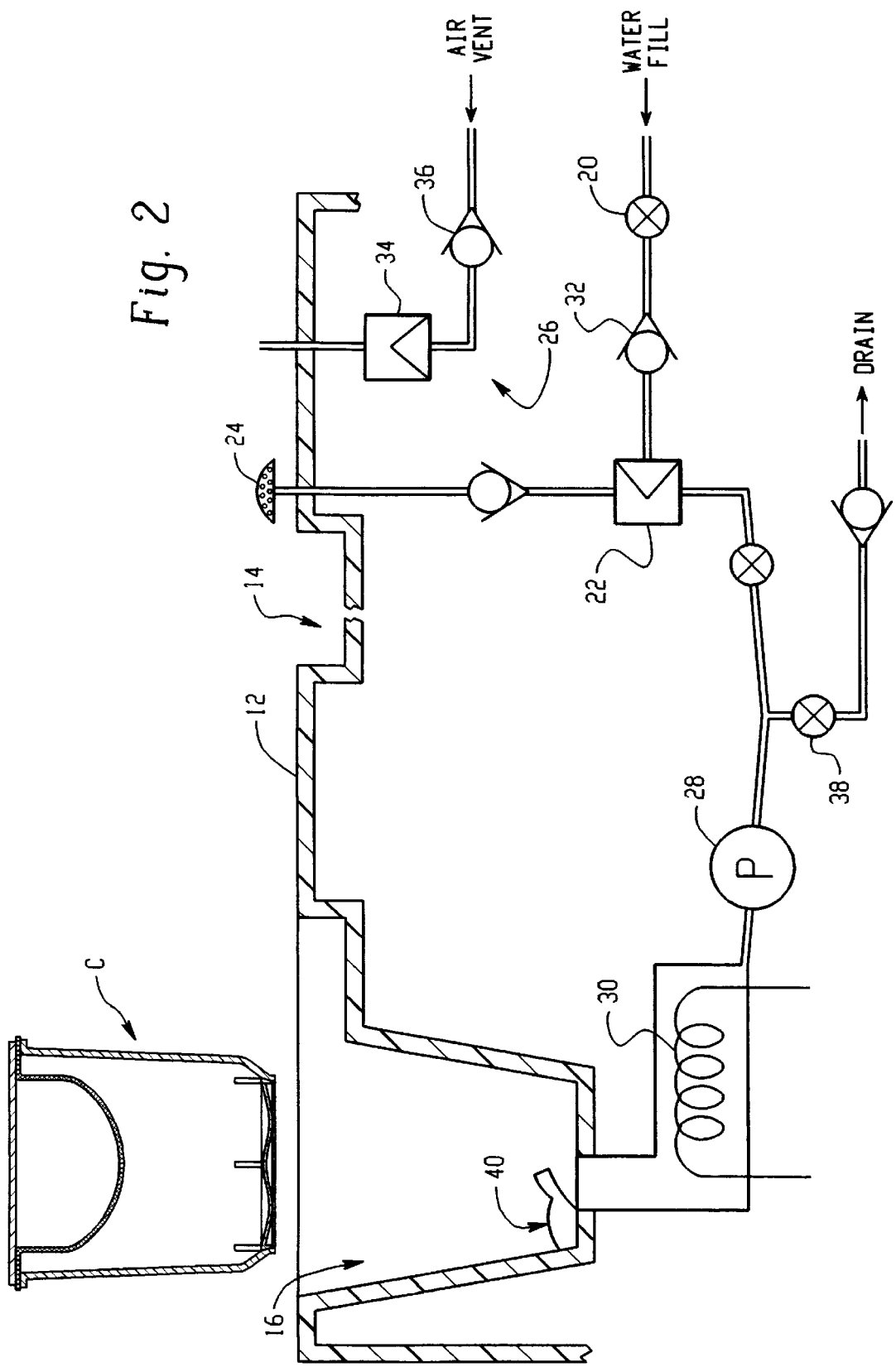
FIG. 2 is a plumbing diagram of the decontamination unit of FIG. 1 including a detailed, cross-sectional view of a reagent cup receiving well and a two-compartment reagent cup.

With reference to FIG. 1 and 2, a microbial decontamination apparatus A is configured to sit on a counter top or other convenient work surface. A door or lid 10 is manually openable to provide access to a tray 12 which defines a receiving region 14 for receiving items to be microbially decontaminated. In the illustrated embodiment, the tray 12 is configured to receive endoscopes or other long, coilable items. Other trays with item receiving regions of different configurations for receiving the items themselves or item holding containers are also contemplated. A well 16 receives a unit dose of reagents for forming a sterilant, disinfectant, or other microbial decontaminating solution.

With particular reference to FIG. 2, a reagent containing package C is inserted into the well 16. Once the items are loaded into the tray and the reagent carrying package C is inserted into the well 16, the lid 10 is closed and latched. Optionally, a fill valve 20 passes water through a microbe removing filter 22 in flow paths of a fluid circulating system. The microbe removing filter 22 provides a source of sterile water by passing water and blocking the passage of all particles the size of microbes and larger. The incoming water which has been sterilized by the filter 22 passes through a spray or distribution nozzle 24 and fills the item receiving region 14 in the tray 12. As additional water is received, it flows into the well 16 dissolving powdered, crystalline, or other non-liquid reagents in the cup C, forming an anti-microbial solution. Filling is continued until all air is forced through an air system 26 and an entire interior volume is filled with the sterile water. After the fill valve 20 is closed, a pump 28 circulates the fluid through a heater 30, the item receiving region 14 of the tray 12, and the well 16. The pump also forces the anti-microbial solution through the filter 22 to a check valve 32 sterilizing the filter. Further, the pump forces the anti-microbial solution through another microbe filter 34 in the air system 26 to a check valve 36. After the anti-microbial solution has been brought up to temperature and circulated for a selected duration, a drain valve 38 is opened, allowing the solution to drain. Air is drawn through the microbe filter 34 such that sterile air replaces the fluid within the system. Thereafter, the drain valve is closed and the fill valve 20 opened again to fill the system with a sterile rinse fluid. It will be noted, that because the pump 28 circulated the anti-microbial solution over all surfaces of the flow paths including all surfaces leading from the sterile rinse source 22, the rinse cannot bring microbial contaminants into the item receiving region 14.

A lower opener projection or member 40 is disposed at the bottom of the well for engaging a lower surface of the package C as it is inserted into the well.

Figure 3:
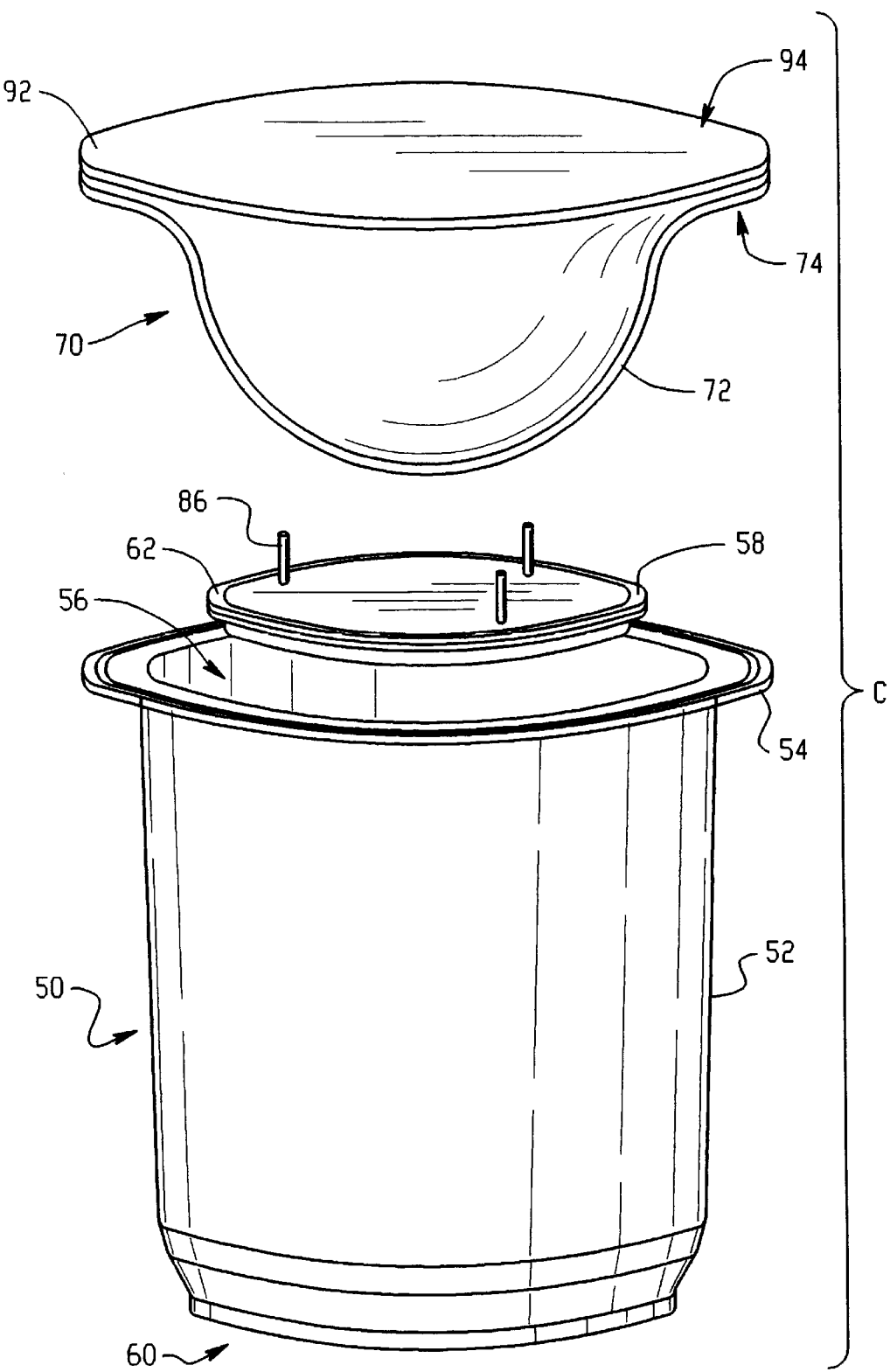
FIG. 3 is an expanded view of a two compartment cup in accordance with the present invention; and, FIG. 4 is a side sectional view of the two compartment cup.
Figure 4:
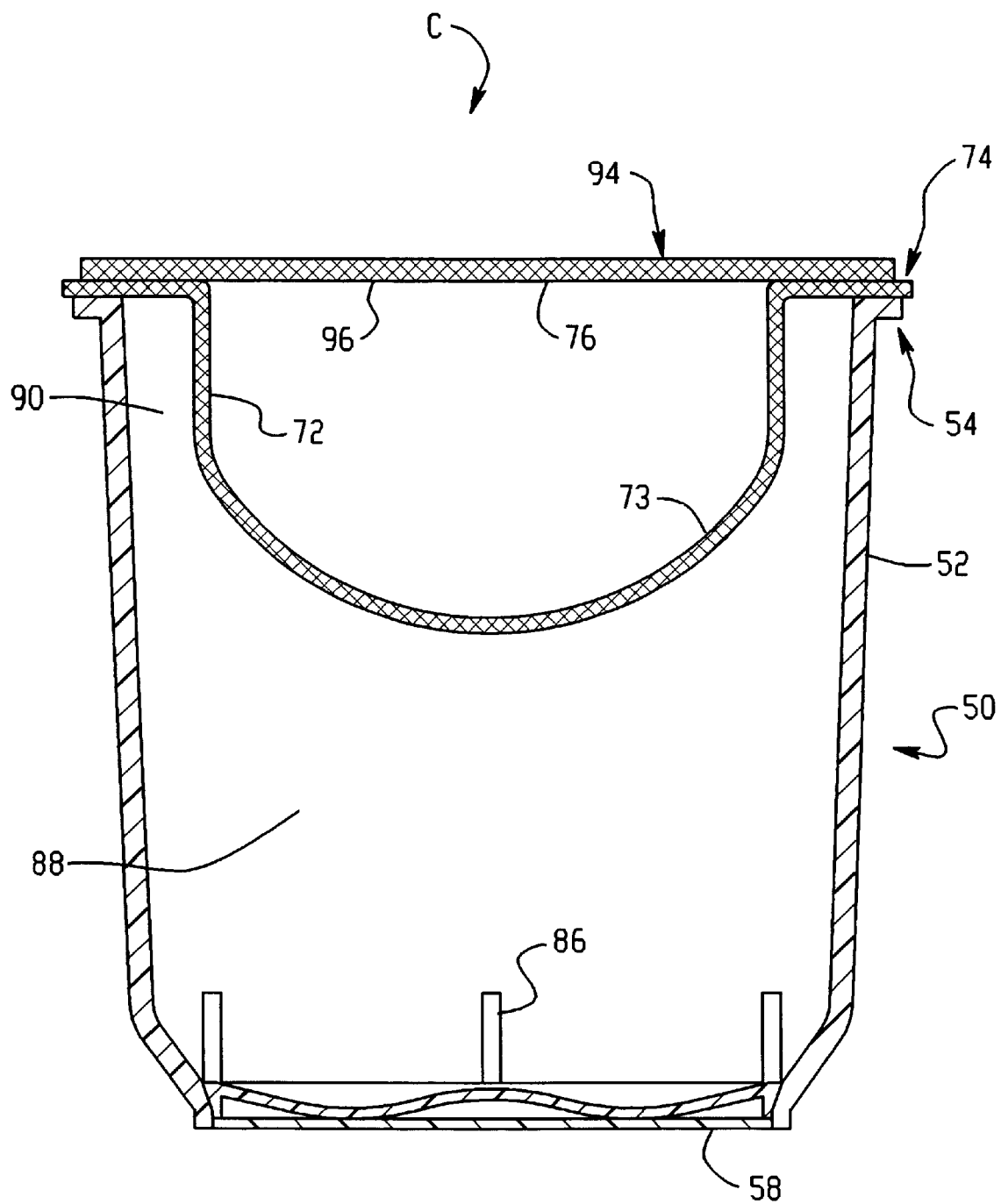

With reference to FIGS. 3 and 4, the sterilant cup or package C includes a first or outer cup 50. The outer cup is constructed of a light weight, rigid polymeric material. The outer cup 50 includes a cylindrical peripheral wall 52 that has a flange 54 at a first, open end 56 thereof. A closure which is impermeable to a reagent disposed in the outer cup, such as a detachable base wall 58, closes a second, opposite end 60 of the peripheral wall 52. The detachable base wall 58 is secured to the second end by being snapped in and held by a lip and groove, friction engagement, a breakable seal, or the like. When force or pressure is applied to the detachable base wall from beneath the outer cup 50 by the lower opener member 40, the detachable base wall 58 detaches. An enlarged flange 62 or the like retains the base wall in the interior of the outer cup by making the diameter of the base wall larger than the opening at the second end.

Figure 5:
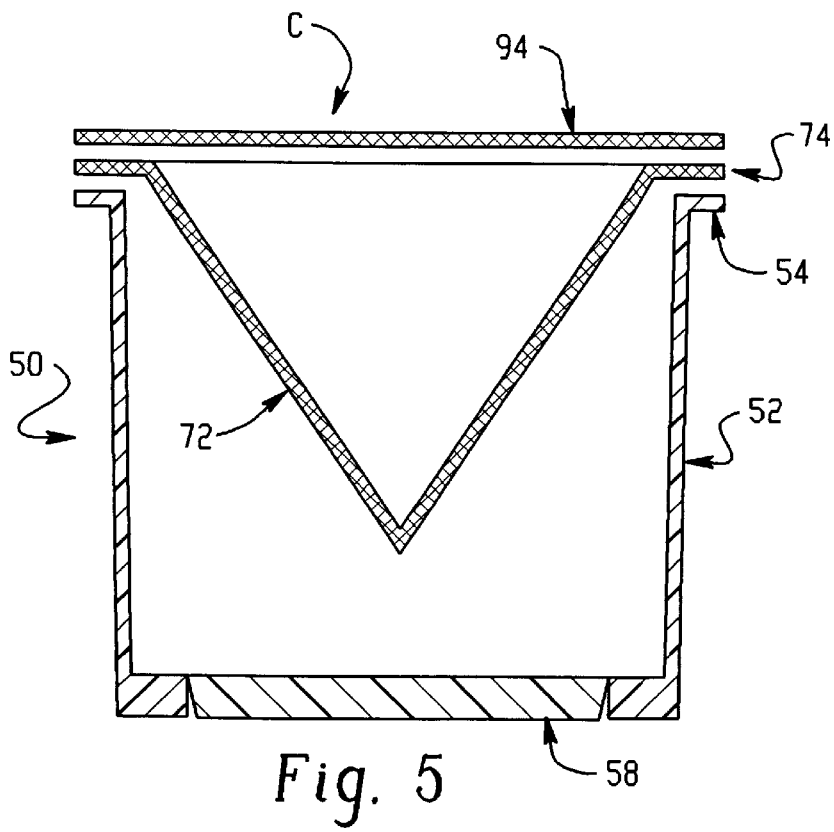
FIG. 5 is an alternate embodiment of the cup of FIG. 3.
Figure 6:
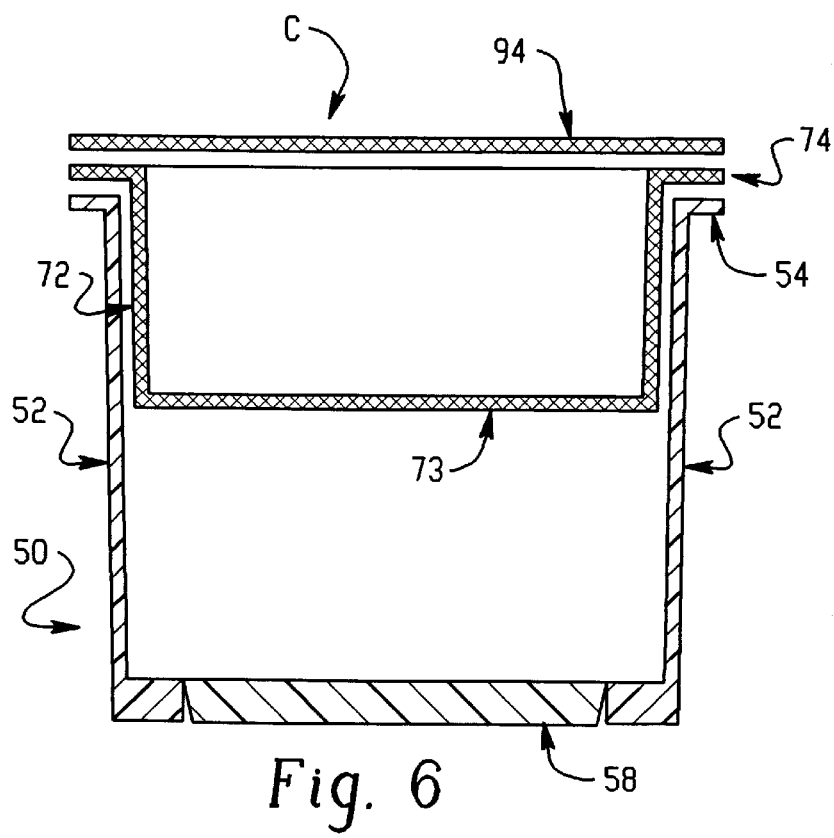
FIG. 6 is another alternate embodiment of the cup of FIG. 3.

A second or inner cup portion 70 is received in the first cup portion 50. The second cup portion has a generally thermally molded, hemispherical peripheral wall 72 that has an integrally molded flange 74. Alternatively, the second cup peripheral wall is cone or cylindrically shaped as shown in FIGS. 5 and 6. The second cup portion is sealed at a first or top end by a top cover 94.

The peripheral wall 72 of the second cup portion 70 and top cover 94 are preferably formed from a material that is impermeable to the dry reagent contained within the first and second cup portions, yet is permeable to water and to dissolved reagents. Alternatively the peripheral wall 72 includes a region 73 that is formed from a material which is impermeable to powdered reagents but which is permeable to water and to dissolved reagents. A similar region is optionally included in the top cover (not shown). Any particles of reagent in the second cup portion 70 that are not dissolved are therefore trapped within the second cup portion. Dissolved reagents pass through the material and are transported to the items to be sterilized.

The choice of material depends on the particle size of the reagents. For reagents having a particle size of about 50 microns, a non-woven polypropylene web or felt keeps the dry reagents from penetrating the material, while allowing the water and dissolved reagents to pass freely through the second cup portion and top cover. When the material is a polypropylene web, the top cover is readily sealed to the second cup portion by ultrasonically welding or other heat sealing the flange of the second cup portion to the top cover.

The material for the second cup portion and top cover is preferably free of additives, such as binders or surfactants, that could be dissolved in the water and contaminate the items to be decontaminated. The material is also preferably lint free, so that small particles of the material do not come away from the second cup and become trapped within items to be decontaminated. Further, the material preferably has a fairly high tensile strength and does not disintegrate when it is subjected to a fairly high pressure of water. The material is also preferably unreactive toward the reagents and other additives used in the decontamination unit. An extruded spun-bonded polypropylene web having an absolute pore size of under 50 microns, and preferably around 10 microns, is a preferred material because it is virtually lint-free. It also has a high tensile strength, even when under a moderately high water pressure. The material is preferably molded to the shape of the inner cup portion 70 from a single sheet of the polypropylene web. Alternatively, the flange 74 is formed from a separate material which is then welded to the remainder of the upper cup portion. The porous nature of the inner cup portion and top cover 94 allows gases formed from the reagents during transit to out gas from the cup C.

Optionally, the material also acts as a filter for filtering particles, such as microorganisms and dirt, from the anti-microbial solution passing through the cup.

The detachable base wall 58 has a domed central region. The domed central region is surrounded by a vertical wall that frictionally engages the peripheral wall of the cup. As force is applied to the domed central region, it flexes. The flexing urges the attached vertical wall away from the peripheral wall of the cup producing the frictional engagement and facilitating its release. Optionally, a plurality of legs 86 or other spaced projections are provided on the base wall.

With continuing reference to FIGS. 3 and 4, the first and second cup portions are configured such that the flanges 54, 74 abut and are sealed together. Appropriate sealing means for the flanges include heat welding, adhesive bonding, solvent welding, ultrasonic welding, or the like. When the inner cup portion and top cover are constructed of a spun-bonded polypropylene and the outer cup portion is also formed from polypropylene, the top cover, inner cup portion, and outer cup portions are preferably ultrasonically or heat welded together at the same time, thereby forming a seal which extends from the top cover and through the flange on the inner cup portion to the flange on the outer cup portion.

Preferably, the inner cup peripheral wall 72 is about half the height of the outer cup peripheral wall 52 such that a first reagent chamber 88 is defined therebetween. More specifically to the illustrated embodiment, the chamber 88 has a predetermined volume ratio relative to a volume of the inner cup 70. Although various second cup peripheral wall designs may be utilized to achieve the selected relative volume ratio between the chamber 88 and the second cup volume, a hemispherical wall surface is conveniently manufactured.

In the preferred embodiment, the inner and outer cups each contain one of an acid precursor and a persalt. More specifically to the preferred embodiment, the acid precursor is acetylsalicylic acid and the persalt is sodium or other perborates. The two compounds dissolve as water flows through the cup. The dissolved compounds come into contact and react to form sodium perborate, peracetic acid, and salicylic acid.

The volume of powdered ingredients is selected relative to the volume of water such that a 0.2% weight/volume concentration of peracetic acid is achieved in the resultant decontamination solution. The sodium perborate solution functions as an inorganic corrosion inhibitor and the salicylic acid is an organic corrosion inhibitor. Preferably, additional corrosion inhibitors, buffers, and a wetting agent are added to these powders. Preferred copper and brass corrosion inhibitors include azoles, benzoates, other five-membered ring compounds, benzotriazoles, tolytriazoles, mercaptobenzothiazole, and the like. Other anti-corrosive buffering compounds include phosphates, molybdates, chromates, dichromates, tungstates, vanadates, other borates, and combinations thereof. These compounds are effective for inhibiting steel and aluminum corrosion. For hard water, in which calcium and magnesium salts may tend to precipitate, a sequestering agent such as sodium hexametaphosphate is also included. Other dry formulations can be utilized to generate chlorine gas, hydrogen peroxide, hypochlorous acid, and other strong oxidants which have a biocidal effect.

To assemble the cup C, the base 58 is first installed in the outer cup portion 50. The first reagent is then disposed within the outer cup portion. The inner cup portion 70 is then placed within the outer cup portion with the flange 74 of the inner cup portion resting on the flange 54 of the outer cup portion. The second reagent is disposed within the inner cup portion and the top cover 94 disposed so that it rests on the flange of the inner cup portion. The top cover, inner cup portion and outer cup portion are then sealed together at the flanges of the inner and outer cup portions. Thus, the first reagent is sealed within the outer cup, while the second reagent is sealed within the inner cup.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A multi-compartment package for holding powdered reagents which interact with water to form an anti-microbial solution, the package including:
   a) an outer, first cup portion having a first peripheral wall which has a first opening at a first end and a second opening at a second end, a detachable base portion secured to the second end of the outer first cup portion and closing the second opening, the detachable base portion being detachable by applying a force to the detachable base portion;
   b) an inner, second cup portion having a second peripheral wall, an overhanging flange connected at an upper end thereof, a top cover at least partially covering the flange, the first and second cup portions being configured such that the second cup portion flange abuts and is connected to the first end of the outer first cup portion, the first and second cup portions being configured such that a first reagent receiving chamber is defined in the first cup portion and a second chamber is defined in the second cup portion, the second cup portion including:
      at least a region which separates the first reagent receiving chamber from the second reagent receiving chamber being formed from a material which is impermeable to the received reagents but is permeable to water and to solutions containing dissolved reagents, such that reagents held in one of the first and second reagent receiving chambers can be dissolved in water, pass through the region to the other of the first and second reagent receiving chambers and react with the reagents therefrom.

2. A two compartment package for holding dry reagents which interact in water to form an anti-microbial solution, the package comprising:
   an outer first cup portion having a first peripheral wall which has a first opening at a first end and a second opening at a second end;
   an inner second cup portion having an overhanging flange connected at one end thereof, the second cup portion including at least a region of a filter material which is permeable to water and solutions, a first reagent receiving chamber defined in the first cup portion and a second chamber defined in the second cup portion, the filter material holding first dry reagents without passing the first dry reagents from the first chamber to the second chamber and without passing second dry reagents from the second chamber to the first chamber, one of the chambers holding an acid precursor and the other chamber holding a persalt, the region of filter material defining a liquid flow path between the first and second chambers for passage of water and a solution containing at least one of the acid precursor and the persalt.

3. The package of claim 2, further comprising a detachable first base portion secured to and closing the second opening at the second end of the outer first cup portion, the first detachable base portion being releasable by applying a force to the detachable first base portion.

4. The package of claim 2, wherein the acid precursor includes acetylsalicylic acid and the persalt includes sodium perborate.

5. The package of claim 2 wherein the filter material has a maximum pore size of less than 50 microns and the first and second reagents have minimum particle sizes of greater than 50 microns.

6. A multi-compartment package for holding powdered reagents which interact with water to form an anti-microbial solution, the package including:
   a) an outer, first cup portion having a peripheral wall which has an opening at a first end and at a second end;
   b) an inner, second cup portion having a second peripheral wall and a base wall, at least the second cup portion base wall including a region which is formed from a material which is impermeable to the powdered reagents but is permeable to water and to solutions containing dissolved reagents, the first and second cup portions being configured such that the second cup portion peripheral wall abuts and is connected to the outer first cup portion adjacent the first end of the first peripheral wall, the first and second peripheral walls and the second cup base wall being configured such that a first powdered reagent receiving chamber is defined in the first cup portion for receiving a first reagent and a second powdered reagent receiving chamber is defined in the second cup portion for receiving a second reagent, the base wall of the second cup portion separating the first and second reagents until the reagents are dissolved in water, a closure secured to and closing the second end of the outer first cup portion, the closure being impermeable to the first reagent.

7. The package of claim 6, wherein the closure is detachable from the second end of the outer first cup portion by applying a force to the closure.

8. The package of claim 6, wherein the second cup portion includes a first flange and the first end of the outer first cup portion includes a second flange and wherein the first flange is sealed to the second flange.

9. The package of claim 6, wherein the material is a spun-bonded polypropylene web having an absolute pare size of under 50 microns.

10. The package of claim 6 wherein the material is thermally molded.

11. The package of claim 6, wherein the second cup portion peripheral and base walls define a hemiovoid.

12. The package of claim 6, wherein the second cup portion includes a flange and a top cover which is sealed around an outer edge to the flange.

13. A multi-compartment package for holding dry reagents which interact in water to form an anti-microbial solution, the package including:
   a) a peripheral wall which has an opening at a first end and at a second end;
   b) a top cover which includes a semi-porous region which is formed from a filter material;
   c) a wall with a region which is formed from a filter material which divides an interior of the peripheral wall into a first region between the wall and the top cover and a second region on an opposite side of the wall;
   d) a first dry reagent received in the first region, the first reagent being soluble in water to form a first reagent solution;
   e) a second dry reagent received in the region, the second dry reagent being soluble in water to form a second reagent solution, the first and second reagent solutions reacting to form the anti-microbial solution; and
   f) the filter material of the top cover and the wall being impermeable to the first and second dry reagents but permeable to waters the first and second reagent solutions, and the antimicrobial solution.

14. The package of claim 13, wherein the top cover is formed from a spun-bonded polymeric web.

15. The package of claim 12, wherein the first peripheral wall of the outer cup portion is formed from a first polypropylene material, the inner cup flange and top cover are formed from a second polypropylene material, and wherein the flange and top cover are sealed contemporaneously to the first peripheral wall.

16. The package of claim 15, wherein the first peripheral wall of the outer cup portion includes an outer cup flange, and wherein the inner cup flange and top cover are sealed contemporaneously to the outer cup flange.

17. The package of claim 13, wherein the top cover, second reagent receiving chamber, and second cup portion region form a fluid flow path for ensuring that fluids entering the package contact the second reagent.

18. The package of claim 6, wherein the first reagent includes acetylsalicylic acid and the second reagent includes sodium perborate.

19. A method comprising:
   providing a first cup having a first cup peripheral wall which has an opening at a first end and is closed by a detachable base wall at a second end;
   metering a preselected volume of a first dry reagent into the first cup;
   inserting a second cup into the first cup, the second cup including:
      a flange at one end and a region formed from a material which is impermeable to the first dry reagent and to a second dry reagent but is permeable to water and to solutions containing dissolved reagents, the first and second cups being configured such that when the second cup is inserted into the first cup, the second cup flange abuts the first cup open end and the region defines a fluid flowpath between the first and second cups;
   connecting the second cup flange to the first cup first end;
   metering a preselected volume of the second dry reagent into the second cup;
   sealing a top cover to the second cup flange surrounding the second cup such that the first and second cups are sealed concurrently.

20. The method of claim 19 further including:
   transporting the sealed cups and the contained dry reagents to a site at which decontamination is to be performed;
   applying a force to the detachable base wall to detach the base wall from the first cup;
   dissolving the first and second dry reagents with water and reacting them to form a decontamination solution; and,
   immersing items to be decontaminated in the decontamination solution.

21. A method comprising:
   metering a preselected volume of a first powdered reagent into a first cup having a first cup peripheral wall which has an opening at a first end and a second opening closed by a closure at a second end, the closure being impermeable to the first powdered reagent;
   metering a preselected volume of a second powdered reagent into a second cup having a flange connected at a first end of the second cup and a region formed from a material which is impermeable to the first and second powdered reagents but is permeable to water and to solutions containing dissolved reagents, the first and second cups being configured such that when the second cup is inserted into the first cup, the second cup flange abuts the first cup open end;
   connecting the second cup flange to the first cup first end;
   sealing a top cover to the second cup flange surrounding the second cup; and,
   flowing water into the package so that at least one of the powdered reagents dissolves in the water and is transported in solution through the porous region to mix with the second of the reagents.

22. The method of claim 21, wherein the steps of connecting the second cup flange to the first cup first end and sealing the top cover to the second cup flange are carried out concurrently.

23. The method of claim 22, wherein the steps of connecting the second cup flange to the first cup first end and sealing the top cover to the second cup flange include ultrasonically welding the top cover, second cup flange, and first cup first end together.

24. The method of claim 21 further including:

transporting the sealed cups and the contained powdered reagent to a site at which decontamination is to be performed;

the step of flowing the water including mixing the first and second powdered reagents with water to form a decontamination solution; and, immersing items to be decontaminated in the decontamination solution.

25. The method of claim 24 wherein the closure comprises a detachable base wall and wherein the method further includes applying a force to the detachable base wall to detach the base wall from the first cup.

26. A decontamination system comprising:

a powdered reagent cup receiving well;

a first fluid flow path defined between a water receiving inlet and the reagent cup receiving well to bring water from the inlet to the well to mix with powdered reagents and form a decontaminant solution;

a second fluid flow path being defined for the decontaminant solution from the reagent cup receiving well to a decontamination region for receiving-items to be decontaminated;

a fluid circulator for selectively circulating fluid through the first and second fluid flow paths and among the inlet, the decontamination region, and the reagent cup receiving well;

a multi-chamber powdered decontamination reagent holding cup for insertion into the well, the cup including:

a) an outer, first cup portion having a peripheral wall which has an opening at a first end and at a second end;

b) an inner, second cup portion having a region which is formed from a material which is impermeable to the powdered reagents but is permeable to water and to solutions containing dissolved reagents, the first and second cup portions being configured such that the second cup portion abuts and is connected to the first end of the outer first cup portion, the first and second cups being configured such that a first powdered reagent receiving chamber is defined in the first cup portion for receiving a first reagent and a second powdered reagent receiving chamber is defined in the second cup portion for receiving a second reagent, a closure secured to and closing the second end of the outer first cup portion, the closure being impermeable to the first reagent.

27. A method comprising:

holding a dry acid precursor composition and a dry persalt composition separated by a water permeable filter material;

dissolving the dry compositions in water to form acid precursor and persalt solutions;

passing the water and at least one of the solutions through the filter material, intermixing the acid precursor and persalt solutions;

reacting the intermixed acid precursor and persalt solutions to form an antimicrobial solution.

* * * * *